United States Patent [19]
Sun et al.

[11] Patent Number: 6,121,774
[45] Date of Patent: Sep. 19, 2000

[54] METHOD FOR ELIMINATING RINGING DURING A NUCLEAR MAGNETIC RESONANCE MEASUREMENT

[75] Inventors: Boqin Sun, Sugar Land; Reza Taherian, Stafford, both of Tex.

[73] Assignee: Schlumberger Technology Corporation, Houston, Tex.

[21] Appl. No.: 09/102,719

[22] Filed: Jun. 22, 1998

[51] Int. Cl.[7] .................................................... G01V 3/00
[52] U.S. Cl. ..................... 324/303; 324/300; 324/307; 324/309; 324/322
[58] Field of Search .................................. 324/303, 300, 324/309, 307, 322

[56] References Cited

U.S. PATENT DOCUMENTS

| | | | |
|---|---|---|---|
| 4,717,878 | 1/1988 | Taicher et al. | 324/303 |
| 5,023,551 | 6/1991 | Kleinberg et al. | 324/303 |
| 5,055,787 | 10/1991 | Kleinberg et al. | 324/303 |
| 5,596,274 | 1/1997 | Sezginer | 324/303 |
| 5,712,566 | 1/1998 | Taicher et al. | 324/303 |

FOREIGN PATENT DOCUMENTS

WO 98/43064   10/1998   WIPO.

OTHER PUBLICATIONS

E. Fukushima and S.B.W. Roeder, "Spurious Ringing in Pulse NMR", *33 J. Magn. Res.*, pp. 199–203 (1979).

*Primary Examiner*—Christine K. Oda
*Assistant Examiner*—Brij B. Shrivastav
*Attorney, Agent, or Firm*—John J. Ryberg; Brigitte L. Jeffery

[57] ABSTRACT

The present invention relates generally to a method for eliminating ringing while measuring nuclear magnetic resonance properties of an earth formation traversed by a borehole. The measurement can be made while drilling or using a wireline tool. During a first time period of a single pulse sequence, the measurement includes the desired spin-echoes and the undesired effects, that is, ringing, measurement noise, and baseline shift. During a second time period of the single pulse sequence, the spin-echoes are eliminated but not the undesired effects. Using the signal collected during the second time period, the signals measured during the first time period are corrected to eliminate the ringing component, measurement noise, and baseline shift.

16 Claims, 4 Drawing Sheets

METHOD FOR ELIMINATING RINGING DURING A NUCLEAR MAGNETIC RESONANCE MEASUREMENT

BACKGROUND OF THE INVENTION

The present invention relates generally to a method for measuring nuclear magnetic resonance properties of an earth formation traversed by a borehole, and more particularly, to a method for eliminating any ringing, such as magnetoacoustic ringing, during a nuclear magnetic resonance measurement.

Borehole nuclear magnetic resonance measurements provide different types of information about a reservoir. First, the measurements provide an indication of the amount of fluid in the formation. Second, the measurements present details about whether the fluid is bound by the formation rock or unbound and freely producible. Finally, the measurements can be used to identify the type of fluid—water, gas, or oil.

One approach to obtaining nuclear magnetic resonance measurements employs a locally generated static magnetic field, $B_0$, which may be produced by one or more permanent or electromagnets, and an oscillating magnetic field, $B_1$, which may be produced by one or more RF antennas, to excite and detect nuclear magnetic resonance to determine porosity, free fluid ratio, and permeability of a formation. See U.S. Pat. Nos. 4,717,878 issued to Taicher et al. and 5,055,787 issued to Kleinberg et al. Nuclear spins align with the applied field $B_0$ with a time constant of $T_1$ generating a nuclear magnetic moment. The angle between the nuclear magnetization and the applied field can be changed by applying an RF field, $B_1$, perpendicular to the static field $B_0$. The frequency of the RF field is equal to the Larmor frequency given by $\omega_0 = \gamma B_0$ where $\gamma$ is the gyromagnetic ratio. After application of an RF pulse, the magnetization begins to precess around $B_0$ and produces a detectable signal in the antenna. The signal detected by the antenna includes a parasitic, spurious ringing that interferes with the measurement of spin-echoes.

The source of the spurious signal is electromagnetic generation of ultrasonic standing waves in metal. See E. Fukushima and S. B. W. Roeder, *Spurious Ringing in Pulse NMR*, 33 J. MAGN. RES. 199–203 (1979). As explained in the Fukushima et al. article, the induced RF current within the skin depth of the metal interacts with the lattice in a static magnetic field through the Lorenz force and the coherent ultrasonic wave propagates into the metal to set up a standing wave. A reciprocal mechanism converts the acoustic energy, in the presence of the static field, to an oscillating magnetic field which is picked up by the antenna as a spurious, ringing signal.

Different types of magnetoacoustic interaction may produce a parasitic signal in the NMR antenna. Antenna wiring and other metal parts of the NMR logging tool can be affected by the static magnetic field and the RF field generated by the antenna. If the antenna is located within the strongest part of the magnet's field, when RF pulses are applied to the antenna, acoustic waves are generated in the antenna and the antenna sustains a series of damped mechanical oscillations in a process known to those skilled in the art as magnetoacoustic ringing. This ringing can induce large voltages in the antenna which are superimposed with the measurement of the voltages induced by the spin-echoes.

Another source of magnetoacoustic interaction is magnetorestrictive ringing which is typically caused when non-conductive magnetic materials, such as magnetic ferrite, are used in the antenna. If this magnetic material is located within the strong part of the RF field, application of RF pulses will generate acoustic waves in the magnet. The magnet will experience a series of damped mechanical oscillations upon cessation of the RF pulse. Magnetorestrictive ringing can also induce large voltages in the antenna which are superimposed with the measurement of the voltages induced by the spin-echoes.

One type of NMR well logging apparatus which reduces magnetoacoustic interaction is described, for example, in U.S. Pat. No. 5,712,566 issued to Taicher et al. The apparatus disclosed in the '566 patent includes a permanent magnet composed of a hard, ferrite magnet material that is formed into an annular cylinder having a circular hole parallel to the longitudinal axis of the apparatus. One or more receiver coils are arranged about the exterior surface of the magnet. An RF transmitting coil is located in the magnet hole where the static magnetic field is zero. The transmitting coil windings are formed around a soft ferrite rod. Thus, magnetoacoustic coil ringing is reduced by the configuration of the transmitting coil. Magnetorestrictive ringing of the magnet is reduced because the radial dependence of the RF field strength is relatively small due to use of the longitudinal dipole antenna with the ferrite rod. Further, magnetorestrictive ringing is reduced because the receiver coil substantially removes coupling of the receiver coil with parasitic magnetic flux due to the inverse effect of magnetorestriction.

The apparatus disclosed in the '566 patent has several shortcomings. First, the permanent magnet material must be electrically nonconductive so that the antenna used to generate a radio frequency magnetic field can be located in the hole. Second, by placing the antenna in the hole, the efficiency of the antenna is decreased due to the distance from the antenna to the formation. The '566 patent describes an alternative embodiment wherein the magnet hole is radially displaced towards the outer surface of the magnet. In the preferred and alternative embodiments of the '566 patent, locating the antenna in the magnet hole increases the radial distance from the antenna to the volume of investigation in the formation. In cases of substantial borehole rugosity, the volume of investigation may be positioned within the borehole itself rather than wholly within the earth formation.

Normally, magnetoacoustic interaction caused by a 180° pulse of a CPMG sequence is eliminated by a phase alternating pulse sequence. As described, for example, in U.S. Pat. No. 5,596,274 issued to Abdurrahman Sezginer and U.S. Pat. No. 5,023,551 issued to Kleinberg et al., a pulse sequence, such as the Carr-Purcell-Meiboom-Gill (CPMG) sequence, first applies an excitation pulse, a 90° pulse, which causes the spins to start precessing. After the spins are tipped by 90° and start to dephase, the carrier of the refocusing pulses, the 180° pulses, is phase shifted relative to the carrier of the 90° pulse according to the sequence:

$$CPMG(\pm) = 90°_{\pm x}[t_{cp}180°_y t_{cp}\pm echo_j],$$

where the bracketed expression is repeated for j=1, 2, ... J, where J is the number of echoes collected in a single CPMG sequence, and $t_{cp}$ is half of the echo spacing. $90°_{\pm x}$ denotes an RF pulse that causes the spins to rotate by a 90° angle about the ±x-axis (phase alternated). Similarly, $180°_y$ denotes an RF pulse that causes a 180° rotation about the y-axis. The ringing due to the 180° pulse is eliminated by combining a pair of phase alternated CPMG sequences, that is, subtracting the echoes in CPMG(−) from the echoes in the neighboring CPMG (+). Generally, the ringing due to the 90° pulse is ignored. In addition to ringing, the electronic measuring circuit may introduce a baseline shift which makes the measurement of the absolute echo intensity more difficult. The phase alternated pulse sequence operation also cancels the spurious baseline that may be present in the measurements.

A drawback to the phase alternated sequence is the requirement to measure two pulse sequence cycles. Measurements made by an NMR logging tool in this manner are therefore subjected to degradation in the vertical resolution due to the logging speed, wait time between each pulse sequence, and the data acquisition time. In addition, the logging tool moves along the longitudinal axis of the borehole between each of the measurements. Possibly, the echoes from the CPMG(±) sequences are measured with the tool facing different formations wherein each formation has a different conductivity. Laboratory tests show that magnetoacoustic interaction is affected by the formation conductivity.

FIGS. 1a–1c present the experimental results of an NMR measurement where the phase alternated pulse sequences are measured at two different conductivities. The positive phase cycle measurement (FIG. 1a) is obtained from a 0.25 Ω-m water sample and the negative phase cycle measurement (FIG. 1b) is obtained from a 0.9 Ω-m water sample. FIG. 1a shows the positive phase echoes, baseline offset, and minimum ringing from the 180° pulse while FIG. 1b illustrates the negative phase echoes, baseline offset, and substantial ringing from the 180° pulse. When these signals are combined by subtracting the signal obtained during the negative phase cycle from the signal obtained during the positive phase cycle, the result depicted in FIG. 1c is obtained which shows that the ringing and baseline offset are not completely canceled with the phase alternated pulse sequences.

SUMMARY OF THE INVENTION

The above disadvantages of the prior art are overcome by means of the subject invention encompassing a method for eliminating ringing while measuring a nuclear magnetic resonance property of earth formations surrounding a borehole. A static magnetic field is applied to a volume of the formation which polarizes the spin nuclei within the volume of formation. An oscillating magnetic field is applied to the volume of formation according to a selected pulse sequence for a plurality of cycles so that a nuclear magnetic resonance signal is generated in the volume of formation. During a first time period of a single pulse sequence cycle, a first plurality of oscillating pulses are applied to the volume of formation and signals generated in the formation are measured. The measured signals comprise a ringing component and a plurality of spin-echoes. Then, the spin-echoes are eliminated. During a second time period of the single pulse sequence cycle, a second plurality of oscillating pulses are applied to the volume of formation and signals generated in the formation are measured. The measured signals comprise the ringing component and substantially exclude the spin-echoes. The signals measured during the first time period are corrected to eliminate the ringing component.

The signals measured during the second time period may further comprise a plurality of stimulated echoes. During the second time period, the spin-echoes and stimulated echoes may be eliminated by repeatedly applying a short pulse followed by a time delay in order to spoil the stimulated echoes and the spin-echoes. Alternatively, during the second time period, a phase alternated pulse sequence may be applied to spoil the stimulated echoes and the spin-echoes.

The subject invention encompasses a method for eliminating a baseline signal while measuring a nuclear magnetic resonance property of earth formations surrounding a borehole. A static magnetic field is applied to a volume of the formation which polarizes the spin nuclei within the volume of formation. An oscillating magnetic field is applied to the volume of formation according to a selected pulse sequence for a plurality of cycles so that a nuclear magnetic resonance signal is generated in the volume of formation. During a first time period of a single pulse sequence cycle, a first plurality of oscillating pulses are applied to the volume of formation and the generated signals in the formation are measured. The measured signals comprise a baseline component and a plurality of spin-echoes. The spin-echoes are eliminated. During a second time period of the single pulse sequence cycle, a second plurality of oscillating pulses are applied in the volume of formation and the generated signals in the formation are measured. The measured signals comprise the baseline component and substantially exclude the spin-echoes. The signals measured during the first time period are corrected to eliminate the baseline component.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

Figure 2:
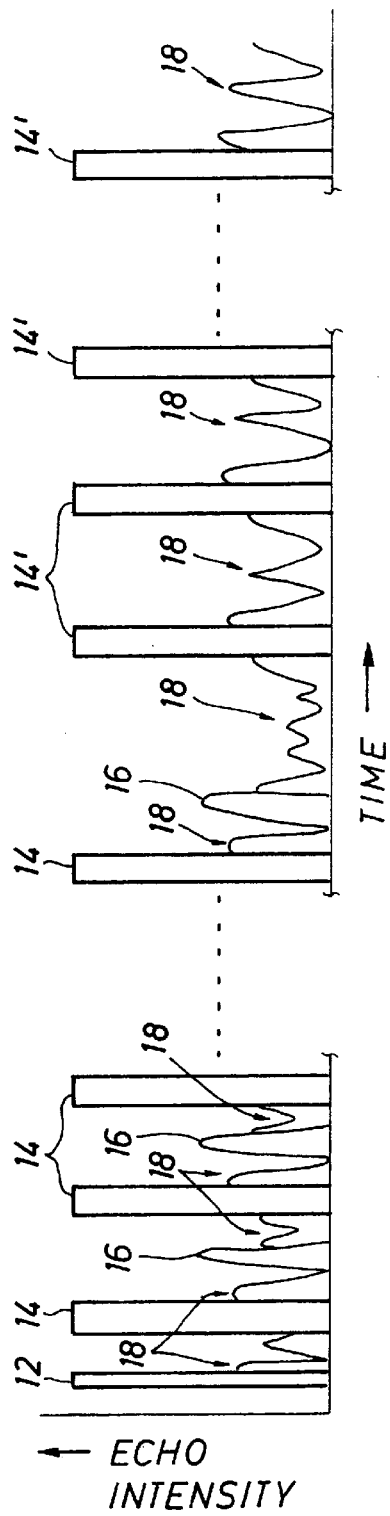
FIG. 2 illustrates the novel pulse sequence in accordance with a preferred embodiment of the present invention.

Referring to FIG. 2, a CPMG pulse-echo sequence is shown which illustrates ringing, such as magnetoacoustic ringing, and the baseline shift present during a nuclear magnetic resonance measurement. Other pulse sequences known to those skilled in the art, such as the Carr-Purcell sequence with inversion (CPI), are within contemplation of this invention. See T. C. FARRAR AND E. D. BECKER, PULSE AND FOURIER TRANSFORM NMR (Academic Press, 1971). The subject invention first measures the desired echo intensity 16 and the undesired effects 18, that is, ringing, measurement noise, and baseline shift, during a single pulse sequence. During the single pulse sequence, the spin-echoes, but not the undesired effects 18, are "spoiled" (i.e., eliminated) using a technique hereinafter referred to as the "RingKiller Approach". After spoiling the spin-echoes during the single pulse sequence, the undesired effects 18 are measured and used to correct the first measured spin-echoes 16 and undesired effects 18 to eliminate the ringing component, measurement noise, and baseline shift in the first measured data. Preferably, the subject invention is used to eliminate ringing due to a 180° pulse, however, it may be used to eliminate ringing from pulses of any length and is not limited to eliminating ringing due to a 180° or even a 90° pulse.

With the RingKiller Approach, a CPMG sequence is executed consisting of an excitation pulse 12 and a sequence of refocusing pulses 14. The measured signal comprises the spin echo 16 and undesired effects 18 consisting of ringing, measurement noise, and baseline shift. The measured signal can be written in the form:

$$S_{nk} = S_{echo,n}(k\Delta t) + R_{180,n}(k\Delta t) + S_{noise,n}(k\Delta t) + d.c. \text{ for } 1 \leq n \leq N_1 \text{ and } 1 \leq k \leq M \quad (1)$$

and $$S'_{nk} R_{180,n}(k\Delta t) + S_{noise,n}(k\Delta t) + d.c. \text{ for } N_1+1 \leq n \leq N_2 \text{ and } 1 \leq k \leq M \quad (2)$$

where $S_{echo,n}(t)$ denotes the $n^{th}$ echo signal, $R_{180,n}(t)$ is the corresponding ringing signal, $S_{noise}(t)$ is measurement noise, d.c. is the baseline offset, $\Delta t$ is the dwell time, $N_1$ is the number of periods where the echo 16 is present, $N_2$ is the total number of periods in the experiment, and M is the number of samples per echo period. Eq. 1 describes the signal before spoiling the spin-echoes while Eq. 2 represents the signal after spoiling the spin-echoes. The averaged ringing signal after spoiling the spin-echoes is:

$$\overline{R}_{180,k} = \frac{1}{N_2 - N_1} \sum_{N_1+1}^{N_2} S'_{nk} \text{ for } 1 \leq k \leq M. \quad (3)$$

The averaged ringing signal comprises the undesired effects 18 of ringing, noise, and baseline shift, provided the tool electronics remain stable during the measurement. With the RingKiller Approach, the measured data, $S_{nk}$, is corrected for the undesired effects 18 according to the following equation:

$$S_{RK,nk} = S_{nk} - \overline{R}_{180,k} = S_{echo,n}(k\Delta t) + S_{noise,n}(k\Delta t) \text{ for } 1 \leq n \leq N_1 \text{ and } 1 \leq k \leq M. \quad (4)$$

Figure 3:
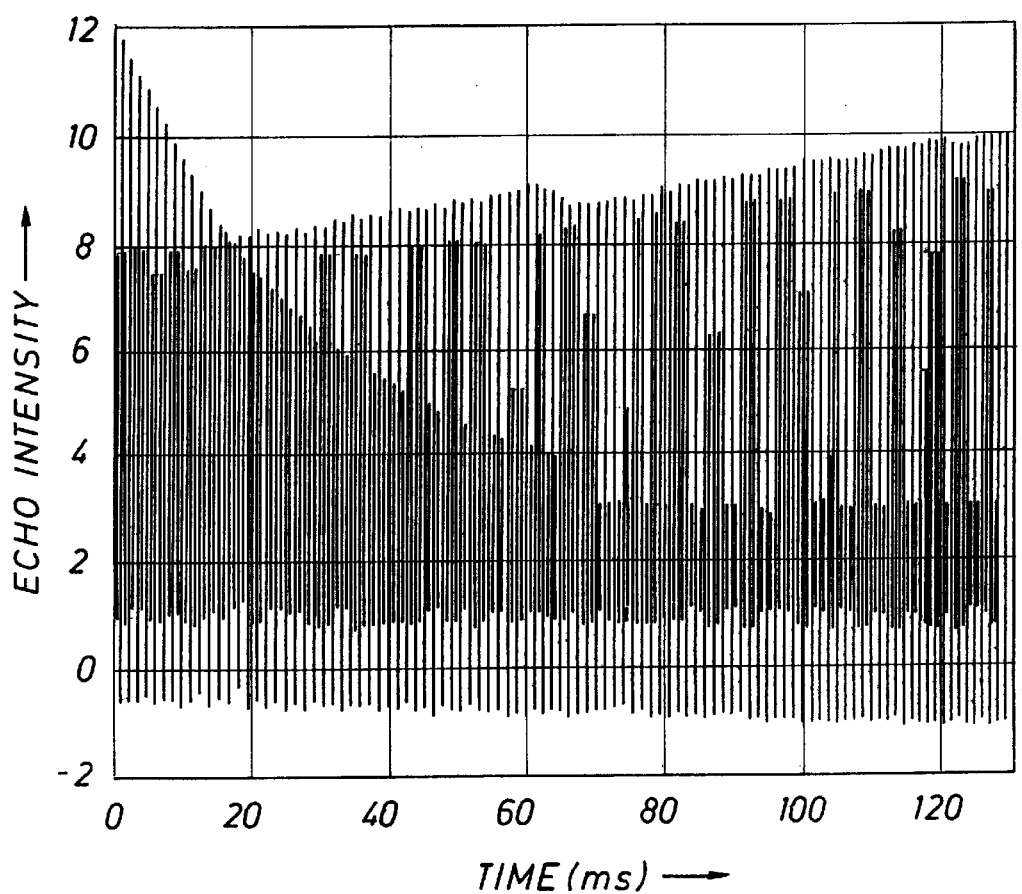
FIG. 3 illustrates the laboratory data obtained as a result of applying the novel pulse sequence to an NMR measurement; and, FIGS. 4a–4b compare the RingKiller corrected data with the phase alternated pulse sequence corrected data.

The electronic circuitry used to obtain a nuclear magnetic resonance measurement may be subject to temperature instability in a high temperature environment. FIG. 3 illustrates the effect of temperature instability on NMR data where the high RF power generated during the sequence of refocusing pulses 14 gradually heats up the electronics thereby changing the system response. Still referring to the example of FIG. 3, the amplitude of the ringing signal experiences a linear change during the CPMG sequence. In this particular example, the RingKiller Approach accounts for this linear effect according to the following equation:

$$S_{RK,nk} = S_{nk} - (a+bn)\overline{R}_{180,k} - (1-a-bn)d.c. \text{ for } 1 \leq n \leq N_1 \text{ and } 1 \leq k \leq M \quad (5)$$

where a is the ratio of the first ringing amplitude and the average ringing amplitudes, and b is the slope of the change of ringing intensity. In general, other suitable forms of Eq. 5 may be used to account for non-linear changes.

In a preferred embodiment of the invention, the spin-echoes are eliminated during the time period between $N_1$ and $N_1+1$ using a spoiling technique hereinafter referred to as the "Missing 180° Pulse" method. Referring to FIG. 2, with the Missing 180° Pulse method, echoes 16 and undesired effects 18 consisting of ringing, measurement noise, and baseline shift are recorded for a length of time $T_{CPMG}$ where $N_1$ is the number of periods where the echoes 16 are present. For the $N_1+1$ time period, the refocusing pulse is delayed by at least $2T_E$ (where $T_E$=echo spacing), followed by a number $(N_2-N_1)$ of refocusing pulses 14' separated by $T_E$. The delay is equivalent to missing at least one 180° pulse in the normal pulse sequence. As a result of missing at least one 180° pulse, the spins defocus for at least $1.5T_E$. Then, the spins are set in the focusing direction for only $T_E$ before the next 180° pulse sets the spins in the defocusing direction. The spins do not have an opportunity to completely refocus thereby spoiling any subsequent spin-echoes.

Referring to FIG. 3, the Missing 180° Pulse spoiling method was tested and measured in the laboratory using a water sample containing $NiCl_2$ solution. Due to the temperature instability of the electronic circuitry, the corrected, measured signal using the RingKiller approach is:

$$S_{RK,nk} = S_{nk} - (a+bn)\overline{R}_{180,k} - (1-a-bn)d.c. \text{ for } 0 < t < 64 \text{ msec}$$

where a=0.8, b=0.005, and $$\overline{R}_{180,k} = \frac{1}{N_2 - N_1} \sum_{N_1+1}^{N_2} S'_{nk}$$

for 64<t<120 msec.

Figure 4A:
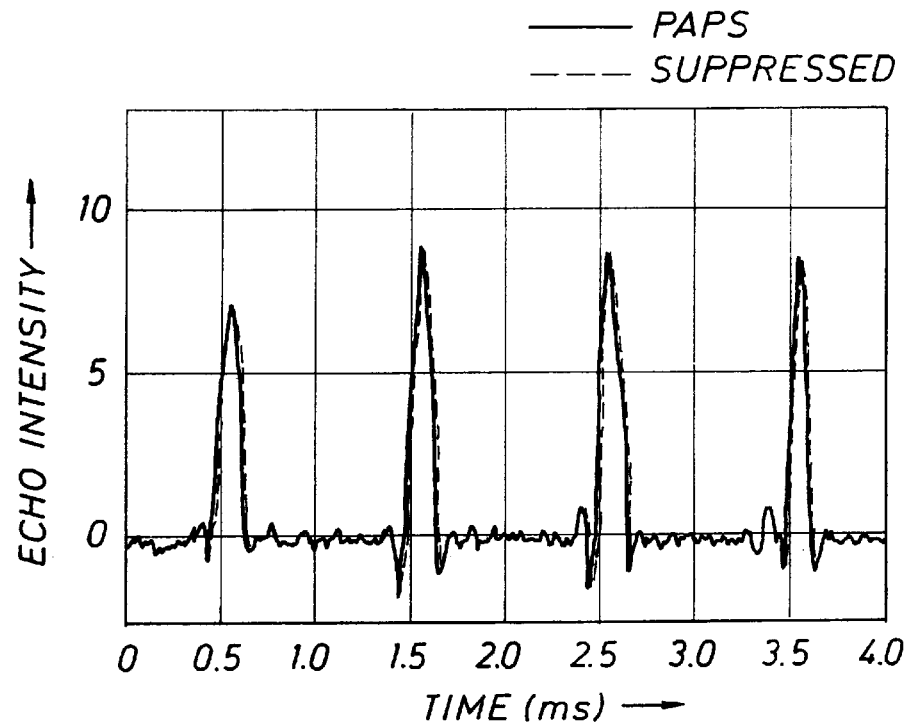
Figure 4B:
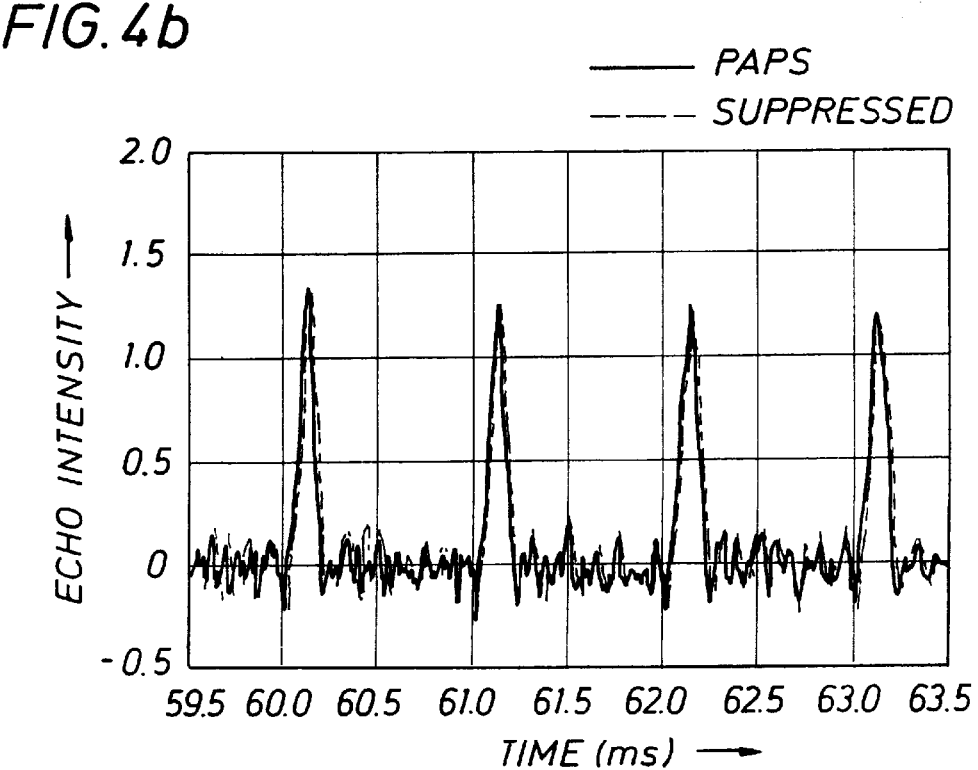

FIGS. 4a–4b compare the RingKiller corrected data with the phase alternated pulse sequence data during the early period (FIG. 4a) when spin-echoes are present (0<t<4 msec) and during a later period (FIG. 4b) when spin-echoes are present (59.5<t<63.5 msec). Laboratory results indicate that the echo shape and intensity obtained from a single pulse sequence using the RingKiller Approach are substantially the same as those obtained from a pair of phase alternated pulse sequences.

Nuclear magnetic resonance measurements respond well to the Missing 180° Pulse spoiling method where the sample has a relatively fast longitudinal relaxation time ($T_1$). For samples having a slower $T_1$, stimulated echoes are produced due to the inhomogeneities in the RF magnetic field. The stimulated echoes are eliminated using various spoiling techniques. During the single CPMG sequence, the stimulated echoes are eliminated by repeatedly applying a short pulse of θ degrees followed by a short time delay, $t_{delay}$. Repeating this sequence randomizes the spins and spoils the stimulated echoes as well as spin-echoes.

Alternatively, the stimulated echoes are eliminated using a phase alternating 180° pulse sequence. During the single CPMG sequence, the stimulated echoes are eliminated by applying a 180° pulse in the (+y) direction followed by a time delay, $t_{delay}$, then application of a 180° pulse in the (−y) direction. Repeating this sequence randomizes the spins and spoils the stimulated echoes as well as spin-echoes. The RingKiller Approach is not limited to the aforementioned spoiling techniques. Other approaches that eliminate the spin-echoes but not the undesired effects are contemplated by this invention.

Figure 1A:
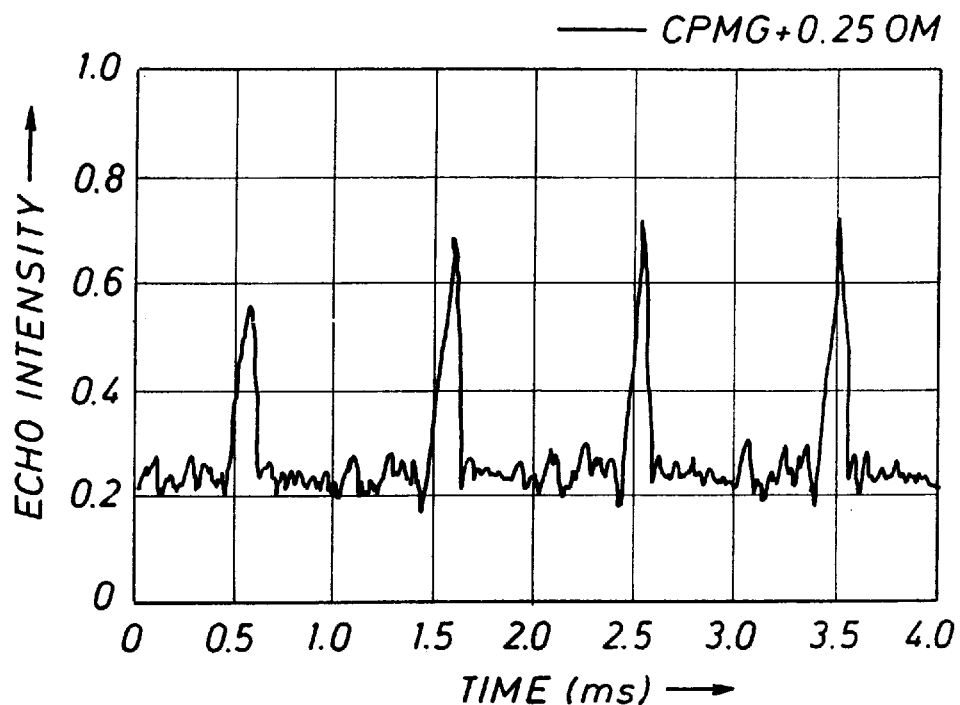
FIGS. 1a–1c depict the effect of formation conductivity on NMR measurements employing a phase alternated pulse sequence.
Figure 1B:
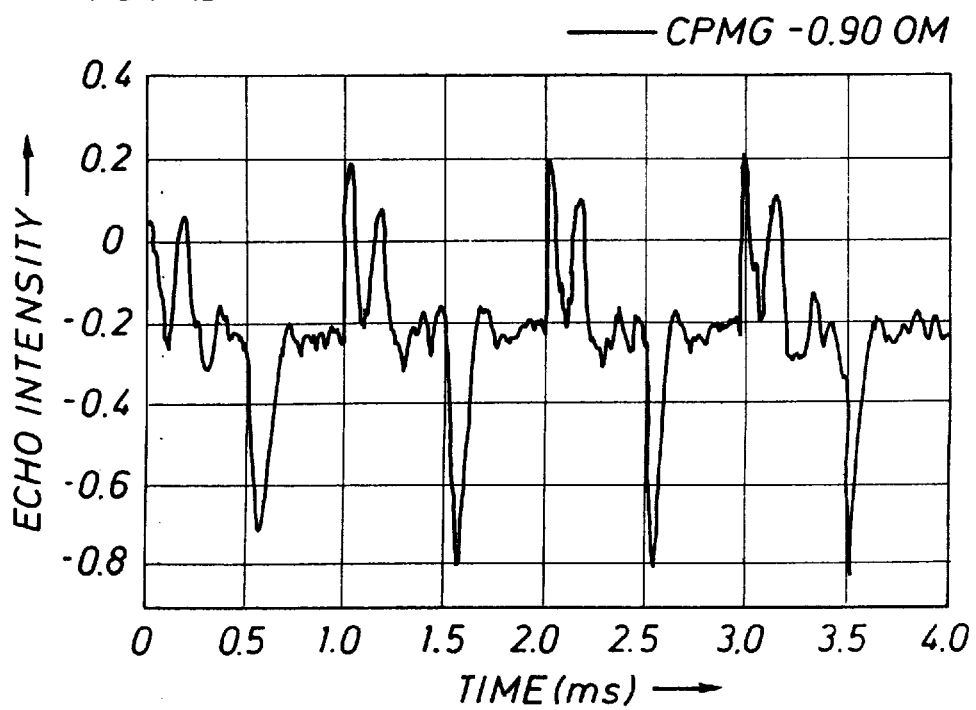
Figure 1C:
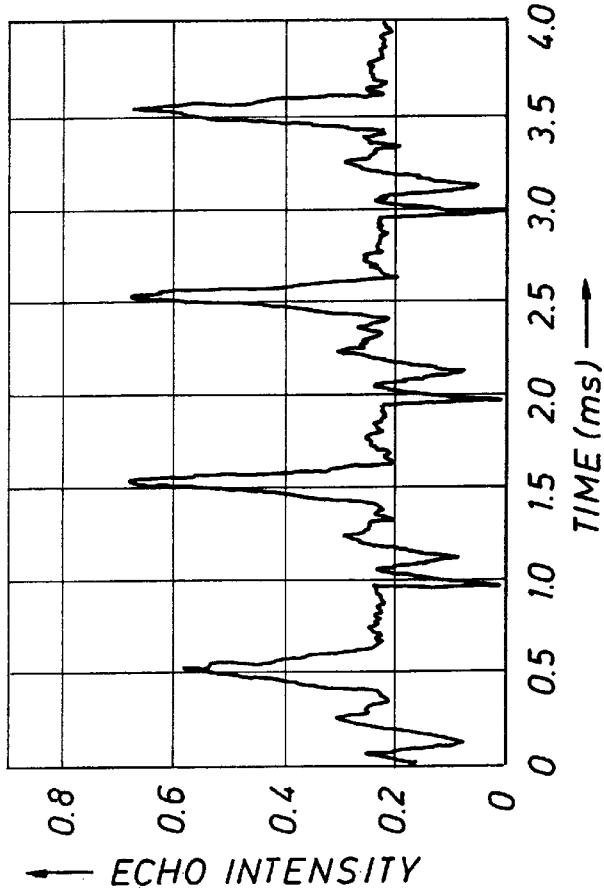

In an alternate embodiment of the invention, the spin-echoes are eliminated by turning off the refocusing pulses after a length of time $T_{CPMG}$ and performing a baseline correction (hereinafter, the "Baseline Approach"). The Baseline Approach is used for a very conductive sample where the undesired effect attributed to ringing is negligible. See FIG 1a. With the Baseline Approach, a CPMG sequence is executed consisting of an excitation pulse and a sequence of refocusing pulses. The measured signal comprises the spin echo and undesired effects consisting of measurement noise, and baseline shift. In the Baseline Approach, the measured signal can be written in the form:

$$S_{nk} = S_{echo,n}(k\Delta t) + S_{noise,n}(k\Delta t) + d.c. \text{ for } 1 \leq n \leq N_1 \text{ and } 1 \leq k \leq M \quad (6)$$

and $$S'_{nk} = S_{noise,n}(k\Delta t) + d.c. \text{ for } N_1+1 \leq n \leq N_2 \text{ and } 1 \leq k \leq M \quad (7)$$

where $S_{echo,n}(t)$ denotes the $n^{th}$ echo signal, $S_{noise,n}(t)$ is measurement noise, d.c. is the baseline offset, $\Delta t$ is the dwell time, $N_1$ is the number of periods where the echo is present, $N_2$ is the total number of periods in the experiment, and M is the number of samples per echo period. After turning off the refocusing pulses, the averaged baseline signal is:

$$\overline{S}_{BL} = \frac{1}{N_2 - N_1} \sum_{N_1+1}^{N_2} S'_{nk} \text{ for } 1 \le k \le M. \qquad (8)$$

The averaged baseline signal comprises the undesired effects of baseline shift provided the tool electronics remain stable during the measurement. With the Baseline Approach, the measured data is corrected for the undesired effects according to the following equation:

$$S_{BL,nk} = S_{nk} - \overline{S}_{BL} = S_{echo,n}(k\Delta t) + S_{noise,n}(k\Delta t) \text{ for } 1 \le n \le N_1 \text{ and } 1 \le k \le M \qquad (9)$$

Further, the measured data may be corrected for the temperature instability of the electronic circuitry in a high temperature environment.

The foregoing description of the preferred and alternate embodiments of the present invention have been presented for purposes of illustration and description. It is not intended to be exhaustive or limit the invention to the precise form disclosed. Obviously, many modifications and variations will be apparent to those skilled in the art.

For example, the subject invention may be used to eliminate ringing due to pulses of any length. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What I claim is:

1. A method for eliminating ringing while measuring a nuclear magnetic resonance property of earth formations surrounding a borehole, comprising the steps of:
   a) applying a static magnetic field in a volume of the formation which polarizes the spin nuclei within the volume of formation;
   b) applying oscillating magnetic fields in the volume of formation according to a selected pulse sequence for a plurality of cycles so that a nuclear magnetic resonance signal is generated in the volume of formation;
   c) during a single pulse sequence cycle, step (b) further comprises the steps of:
      i) during a first time period, applying a first plurality of oscillating pulses in the volume of formation and measuring the generated signals in the formation, the measured signals comprise a ringing component and a plurality of spin-echoes;
      ii) canceling the spin-echoes;
      iii) during a second time period, applying a second plurality of oscillating pulses in the volume of formation and measuring the generated signals in the formation, the measured signals comprise the ringing component and substantially exclude the spin-echoes; and,
      iv) correcting the signals measured during the first time period to eliminate the ringing component.

2. The method of claim 1 wherein the measured signal during the first and second time period further comprises a baseline signal and measurement noise, and the step of correcting the signals measured during the first time period further eliminates the baseline signal.

3. The method of claim 2, further comprising the step of averaging the signals measured during the second time period, and the step of correcting the signals measured during the first time period further comprises the step of combining the averaged signal and the signal from the first period to eliminate the ringing, baseline signal, and measurement noise so that the corrected signal substantially comprises the spin-echoes with minimal added noise.

4. The method of claim 1, wherein the measured signals during the second time period further comprise a plurality of stimulated echoes.

5. The method of claim 4 further comprising the step of correcting the signals measured during the second time period to eliminate the stimulated echoes.

6. The method of claim 5 further comprising the step of repeatedly applying a short pulse followed by a time delay in order to spoil the stimulated echoes.

7. The method of claim 5 further comprising the step of applying a phase alternated pulse sequence to spoil the stimulated echoes.

8. A method for eliminating a baseline signal while measuring a nuclear magnetic resonance property of earth formations surrounding a borehole, comprising the steps of:
   a) applying a static magnetic field in a volume of the formation which polarizes the spin nuclei within the volume of formation;
   b) applying oscillating magnetic fields in the volume of formation according to a selected pulse sequence for a plurality of cycles so that a nuclear magnetic resonance signal is generated in the volume of formation;
   c) during a single pulse sequence cycle, step (b) further comprises the steps of:
      i) during a first time period, applying a first plurality of oscillating pulses in the volume of formation and measuring the generated signals in the formation, the measured signals comprise a baseline component and a plurality of spin-echoes;
      ii) canceling the spin-echoes;
      iii) during a second time period, applying a second plurality of oscillating pulses in the volume of formation and measuring the generated signals in the formation, the measured signals comprise the baseline component and substantially exclude the spin-echoes; and,
      iv) correcting the signals measured during the first time period to eliminate the baseline component.

9. The method of claim 8 further comprising the step of eliminating application of any oscillating pulses during the second time period.

10. The method of claim 1 further comprising the steps of: providing a drilling device, drilling a borehole in the earth formation with the drilling device, and eliminating the ringing while drilling the borehole.

11. The method of claim 8 further comprising the steps of: providing a drilling device, drilling a borehole in the earth formation with the drilling device, and eliminating the baseline signal while drilling the borehole.

12. A method for eliminating ringing while measuring a nuclear magnetic resonance property of earth formations surrounding a borehole, comprising the steps of:
   a) applying a static magnetic field in a volume of the formation which polarizes the spin nuclei within the volume of formation;
   b) applying oscillating magnetic fields in the volume of formation according to a selected pulse sequence for a plurality of cycles so that a nuclear magnetic resonance signal is generated in the volume of formation;

c) during a single pulse sequence cycle, step (b) further comprises the steps of:

i) during a first time period, applying a first plurality of oscillating pulses in the volume of formation and measuring the generated signals in the formation, the measured signals comprise a ringing component, a plurality of spin-echoes, and a plurality of stimulated echoes;

ii) canceling the spin-echoes and the stimulated echoes;

iii) during a second time period, applying a second plurality of oscillating pulses in the volume of formation and measuring the generated signals in the formation, the measured signals comprise the ringing component and substantially exclude the spin-echoes and the stimulated echoes; and, iv) correcting the signals measured during the first time period to eliminate the ringing component.

13. The method of claim 12 further comprising the step of repeatedly applying a short pulse followed by a time delay in order to spoil the spin-echoes and the stimulated echoes.

14. The method of claim 12 further comprising the step of applying a phase alternated pulse sequence to spoil the spin-echoes and the stimulated echoes.

15. The method of claim 12 wherein the measured signal during the first and second time period further comprises a baseline signal and measurement noise, and the step of correcting the signals measured during the first time period further eliminates the baselines signal.

16. The method of claim 15, further comprising the step of averaging the signals measured during the second time period, and the step of correcting the signals measured during the first time period further comprises the step of combining the averaged signal and the signal from the first period to eliminate the ringing, baseline signal, and measurement noise so that the corrected signal substantially comprises the spin-echoes with minimal added noise.

* * * * *